United States Patent
Rey et al.

(10) Patent No.: US 9,488,703 B2
(45) Date of Patent: Nov. 8, 2016

(54) MAGNETIC RESONANCE-COMPATIBLE ELECTRICAL DEVICE WITH RADIO FREQUENCY SHIELDING OR AN ENCLOSURE

(75) Inventors: Eduardo M. Rey, Winter Springs, FL (US); Robert A. Harwell, Saint Cloud, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 925 days.

(21) Appl. No.: 13/509,799

(22) PCT Filed: Nov. 18, 2010

(86) PCT No.: PCT/IB2010/055264
§ 371 (c)(1),
(2), (4) Date: May 15, 2012

(87) PCT Pub. No.: WO2011/070466
PCT Pub. Date: Jun. 16, 2011

(65) Prior Publication Data
US 2012/0242339 A1    Sep. 27, 2012

Related U.S. Application Data (60) Provisional application No. 61/285,204, filed on Dec. 10, 2009.

(51) Int. Cl.
*G01V 3/00* (2006.01)
*G01R 33/28* (2006.01)
*G01R 33/42* (2006.01)
*A61N 1/37* (2006.01)

(52) U.S. Cl.
CPC ............... *G01R 33/28* (2013.01); *G01R 33/42* (2013.01); *A61N 1/3718* (2013.01)

(58) Field of Classification Search
CPC ..................................... G01R 33/42
USPC ................... 324/318, 322, 319, 320
See application file for complete search history.

(56) References Cited

U.S. PATENT DOCUMENTS

| | | | | |
|---|---|---|---|---|
| 5,432,449 | A * | 7/1995 | Ferut et al. | 324/318 |
| 5,592,087 | A | 1/1997 | Richard et al. | |
| 8,323,768 | B2 * | 12/2012 | Connelly et al. | 428/137 |

(Continued)

FOREIGN PATENT DOCUMENTS

| | | |
|---|---|---|
| EP | 0724164 A1 | 7/1996 |
| JP | 11076192 A | 3/1999 |

(Continued)

OTHER PUBLICATIONS

Losito, O.; An Analytical Characterization of Metal Foams for Shielding Applications; 2008; PIERS Online; 4(8) 805-810.

*Primary Examiner* — Louis Arana (57) ABSTRACT

An apparatus comprises an electrical device or component (40) and a radio frequency shield arranged to shield the electrical device or component. The apparatus is disposed in a radio frequency (Bi) field generated by a magnetic resonance scanner and in time varying magnetic field gradients generated by the magnetic resonance scanner (10). The radio frequency shield includes an electrically conductive sheet or layer having openings suppressing time varying magnetic field gradient induced vibration of the radio frequency shield.

22 Claims, 6 Drawing Sheets

(56) References Cited

U.S. PATENT DOCUMENTS

| | | |
|---|---|---|
| 8,779,773 B2 * | 7/2014 | de Lima et al. ............. 324/318 |
| 2004/0251042 A1 | 12/2004 | Weiner et al. |
| 2005/0073308 A1 | 4/2005 | Havens |
| 2005/0104590 A1 | 5/2005 | Sinnema et al. |
| 2008/0051854 A1 | 2/2008 | Bulkes et al. |

FOREIGN PATENT DOCUMENTS

| | | |
|---|---|---|
| JP | 2009119080 A | 6/2009 |
| WO | 2005119284 A1 | 12/2005 |

* cited by examiner

MAGNETIC RESONANCE-COMPATIBLE ELECTRICAL DEVICE WITH RADIO FREQUENCY SHIELDING OR AN ENCLOSURE

CROSS REFERENCE TO RELATED APPLICATIONS

This application claims the benefit of U.S. provisional application Ser. No. 61/285,204 filed Dec. 10, 2009, which is incorporated herein by reference.

The following relates to the magnetic resonance arts, electronics arts, and related arts.

A subject undergoing a magnetic resonance (MR) procedure such as an MR imaging procedure is positioned inside the bore of an MR scanner. A static ($B_0$) magnetic field is generated in the bore, and radiofrequency field ($B_1$) pulses are applied at a magnetic resonance frequency to excite protons in the subject. The MR frequency depends on the nuclear species of interest and the magnetic field strength. As two examples, for $^1H$ excitation the MR frequency is 64 MHz at 1.5 T, and 128 MHz at 3.0 T, respectively. Magnetic field gradients are applied to spatially limit the region of MR excitation, to spatially encode the phase and/or frequency of the magnetic resonance, to extinguish magnetic resonance, or for other purposes. The magnetic field gradients are time varying, but at frequencies substantially lower than the $B_1$ field radio frequency.

Electronic devices that operate inside or near the MR scanner bore, such as patient monitors, are exposed to the static $B_0$ magnetic field, the $B_1$ radiofrequency fields and to the time-varying magnetic field gradients. The static ($B_0$) magnetic field is generated constantly, whereas the $B_1$ radiofrequency field and the magnetic field gradients are generated only during imaging or other MR data acquisition sequences.

MR-compatible electronic devices must operate within designated specifications in the presence of interference caused by the $B_1$ field and magnetic field gradients. The influence of the $B_1$ radiofrequency field can be reduced by employing radio frequency shielding techniques such as soldering an on-board shield to a printed circuit board in order to shield sensitive electronics, using an enclosure to enclose the entire assembly, or so forth. Another benefit of the radio frequency shielding is that it can mitigate radio frequency interference emanating from the electronic device.

The time-varying magnetic field gradients present a fast changing magnetic field that induces eddy currents in conductors. These eddy currents interact with the $B_0$ and other electromagnetic fields in the MR bore and can cause conductors to mechanically vibrate. The eddy currents can also induce heating in the conductors.

The following provides new and improved apparatuses and methods which overcome the above-referenced problems and others.

In accordance with one disclosed aspect, an apparatus comprises an electrical device or component and a radio frequency shield arranged to shield the electrical device or component. The apparatus is disposed in a radio frequency ($B_1$) field generated by a magnetic resonance scanner and in time varying magnetic field gradients generated by the magnetic resonance scanner. The radio frequency shield includes an electrically conductive sheet or layer structure having openings suppressing time varying magnetic field gradient induced vibration of the radio frequency shield.

In accordance with another disclosed aspect, an apparatus comprises an electrical device or component and an enclosure enclosing the electrical device or component. The apparatus is disposed in a radio frequency ($B_1$) field generated by a magnetic resonance scanner and in time varying magnetic field gradients generated by the magnetic resonance scanner. The enclosure includes an electrically conductive sheet or layer having openings suppressing time varying magnetic field gradient induced vibration of the enclosure.

In accordance with another disclosed aspect, a magnetic resonance system comprises: a magnetic resonance scanner including a main magnet generating a static ($B_0$) magnetic field in an examination region, magnetic field gradient windings for superimposing time varying magnetic field gradients in selected directions within the examination region, and one or more radio frequency coils for generating a radio frequency ($B_1$) field in the examination region; and an apparatus as set forth in any one of the two immediately preceding paragraphs disposed in the radio frequency ($B_1$) field generated by the magnetic resonance scanner and in the time varying magnetic field gradients generated by the magnetic resonance scanner.

One advantage resides in providing electronic components that are less susceptible to mechanical vibration in an MR environment.

Another advantage resides in providing reduced conductor heating due to eddy currents in an MR environment.

Another advantage resides in providing reduced opposing magnetic fields to the fields generated by the magnetic resonance system in an MR environment.

Another advantage resides in providing more effective radiofrequency (RF) shielding, and electronic devices with more effective RF shielding, for use in an MR environment.

Further advantages will be apparent to those of ordinary skill in the art upon reading and understanding the following detailed description.

Figure 1:
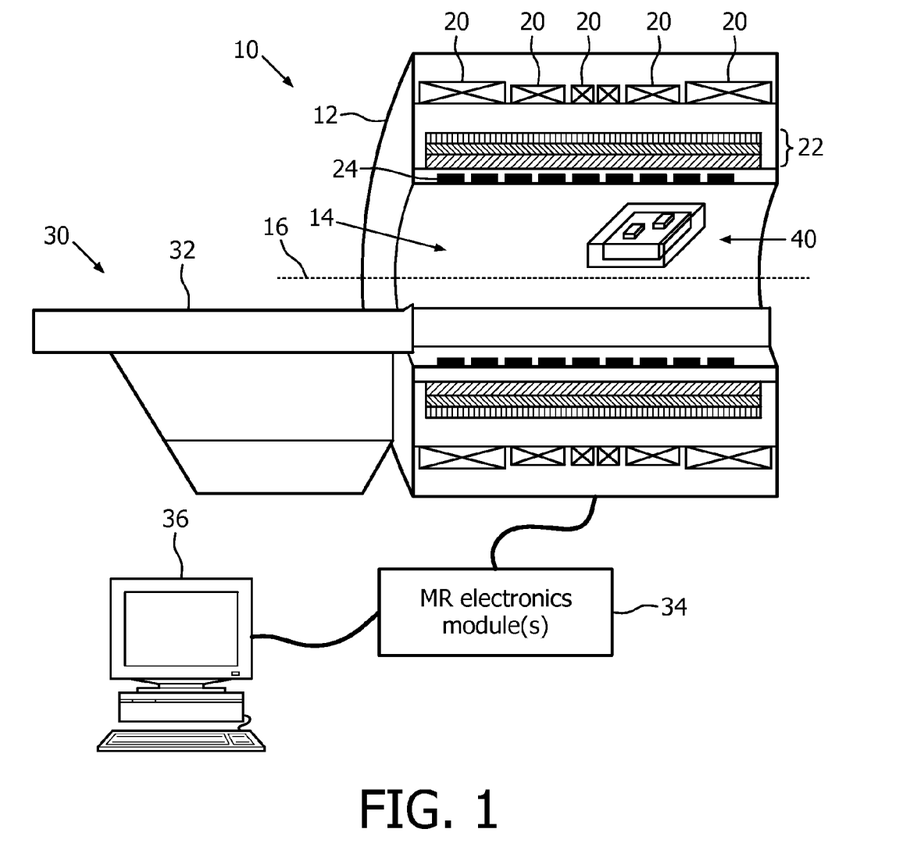
FIG. 1 diagrammatically illustrates a magnetic resonance (MR) system including an MR scanner with a bore and an electronic device or component disposed in the bore, in which the electronic device includes radio frequency shielding as disclosed herein.

With reference to FIG. 1, a magnetic resonance (MR) system includes an MR scanner 10 comprising a generally cylindrical or toroidal housing 12, which is shown in partial cross-section in FIG. 1 to diagrammatically reveal selected internal components. The housing 12 defines a bore 14 that is concentric with a cylinder or toroid axis 16 of the housing 12. A subject is received in the bore 14 for imaging. A main magnet 20 defined by solenoidal conductive windings generates a static ($B_0$) magnetic field with the field direction generally parallel with the cylinder or toroid axis at least within an examination region of the bore 14. The windings of the main magnet 20 may be resistive or superconducting; in the latter case the windings are typically disposed in a cryostat (not shown) containing helium or another suitable cryogenic fluid. Resistive windings may have a cooling arrangement employing water, forced air, or liquid nitrogen as the cooling fluid, for example.

The housing 12 further contains or supports a plurality of magnetic field gradient windings 22 for superimposing magnetic field gradients in selected directions within the examination region of the bore 14. The magnetic field gradients are in general time-varying. As an illustrative example, a slice-selective magnetic field gradient may be applied along the axis 16 of the bore during magnetic resonance excitation to select an axial slice, followed by a quiescent period during which a phase-encoding magnetic field gradient is applied transverse to the axial slice, followed by a readout period during which a frequency-encoding magnetic field gradient is applied in a direction transverse to both the axis 16 and the phase encoding direction. In more complex sequences such as echo-planar imaging (EPI), sinusoidal or other rapidly time-varying magnetic field gradients may be applied by selective energizing of the gradient windings 22.

The magnetic resonance excitation is generated by applying a radiofrequency ($B_1$) pulse at the magnetic resonance frequency (e.g., 128 MHz for $^1H$ excitation in a 3.0 T field) to one or more radio frequency coils 24. In the illustrative embodiment, the radio frequency coil 24 is a "whole-body" volume coil such as a birdcage coil or transverse electromagnetic (TEM) coil arranged on or in the housing 12 concentric with the axis 16. More generally, a local coil or coil array such as a head coil, limb coil, surface coil, or so forth is used for the MR excitation. The MR readout may be performed using the same coil or coils 24 as is used for the excitation, or the MR readout may be performed by a different radio frequency coil or coils (not shown).

In the illustrative embodiment, a patient loading system includes a patient couch 30 arranged at an end of the housing 12 so that a patient on a bed 32 can be transferred into the bore 14 of the MR scanner 10. The couch 30 may be permanently mounted in the illustrated position, or may be a mobile couch having wheels, rollers, or the like to enable the subject to be loaded and then moved and docked with the MR scanner 10. The MR system further includes suitable MR electronic modules 34 for controlling the MR scanner 10 to acquire MR data and to process the acquired MR data. For example, the MR electronic modules 34 may include an image reconstruction module. A computer 36 provides user interfacing with the MR system, and may also embody some or all of the MR electronic modules 34 as software executing on the computer 36.

The illustrative MR scanner 10 is an example. Approaches disclosed herein for reducing detrimental interaction of electrical conductors with the time-varying magnetic field gradients by using electrically conductive material including openings suppressing time-varying magnetic field gradient-induced vibration of the electrical conductor are generally applicable with any type of MR scanner, including the illustrated horizontal cylindrical bore scanner 10, or an open MR scanner, vertical-magnet MR scanner, or so forth.

With continuing reference to FIG. 1, an electronic device or component 40 is diagrammatically shown. The electronic device or component 40 may, for example, be a patient monitoring device such as a physiological monitor (electrocardiograph, respiratory monitor, blood pressure monitor, or so forth). The illustrative electronic device or component 40 is disposed in the bore 14 of the MR scanner 10; however, the electronic device or component configured for use in a magnetic resonance system may be disposed outside the bore 14 (or, more generally, outside the MR examination region, in the case of an open MR scanner or the like) but close enough to the bore or MR examination region to be influenced by the radiofrequency ($B_1$) field and magnetic field gradients.

Figure 1A:
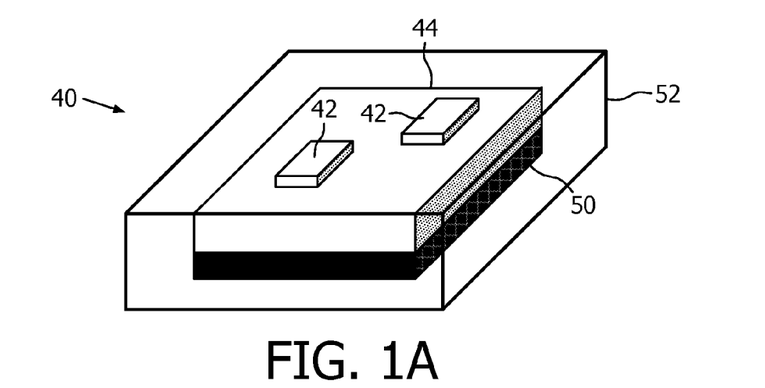
FIG. 1A diagrammatically illustrates an enlarged view of the electronic device or component.

With continuing reference to FIG. 1 and with further reference to FIG. 1A which shows an enlarged view of the electronic device or component 40, the electronic device includes one or more electronic elements 42, such as integrated circuit (IC) chips, sensor devices, passive components such as resistors, capacitors, or inductors, or so forth. In the illustrative embodiment, two representative electronic elements 42 are disposed on a circuit board 44 and are electrically interconnected by electrically conductive traces (not shown) of the circuit board 44. The electronic device or component 40 may optionally include other elements (not shown), such as one or more wired connections with the MR electronic modules 34 or other components located outside the bore 14, or a radiofrequency transceiver for providing wireless connection with same, or so forth.

With continuing reference to FIGS. 1 and 1A, radio frequency shielding is also provided to suppress detrimental influence of the $B_1$ radiofrequency field on the electronic device or component 40, and to suppress radiofrequency (RF) interference emanating from the electronic device or component 40. The illustrative radio frequency shielding includes an electrically conductive ground plane 50 of the circuit board 44 and an electrically conductive enclosure 52 surrounding the electronic device or component 40. It should be noted that the electrically conductive enclosure 52 is typically partially or wholly optically opaque (for example, being made in whole or in part of metal), but is shown in phantom (that is, transparent) in order to show the contained electronic device or component 40 and ground plane 50. In some embodiments, the radio frequency shielding may include only the ground plane 50 (with the enclosure 52 omitted). In some embodiments, the radio frequency shielding may include only the enclosure 52 (with the ground plane 50 omitted). In some embodiments, the ground plane 50 and the enclosure 52 may be a single combined element, for example by having one side of the enclosure also serve as the ground plane for the circuit board. The enclosure 52 (if included) may in general be an on-board enclosure, coffin-style enclosure, or so forth.

In general, conductive radio frequency shielding is susceptible to vibration and eddy current induced heating caused by the magnetic field gradients generated by the gradient coils 22. When eddy currents are induced in radio frequency shielding so as to cause vibration, small voltages or currents are introduced via loop and dipole antenna effects into electrical traces of circuit boards that contain low-amplitude (e.g., microvolt to millivolt level) physiological waveform data. When a diamagnetic material such as copper, which is sometimes used as a radio frequency shielding material, is placed in the path of a changing magnetic field created by a time-varying magnetic field gradient, a small interfering voltage/current is generated that can cause measurement errors or other electronic device errors.

It is disclosed herein to provide radio frequency shielding 50, 52 while simultaneously suppressing eddy currents and their consequent effects such as mechanical vibrations and signal errors, by constructing the radio frequency shielding 50, 52 using one or more meshes (see FIG. 2), or a perforated metal (see FIGS. 3-5), or a conductive sheet constructed of electrically conductive elements joined by small interconnecting electrically conductive tabs (see FIG. 6), or a sheet or layer of generally contacting electrically conductive particles dispersed in an electrically insulating binder (see FIG. 7), or a sheet or layer of interweaved electrically conductive fibers (see FIG. 8), or another arrangement in which the radio frequency shielding 50, 52 comprises electrically conductive material including openings suppressing time-varying magnetic field gradient-induced vibration of the radio frequency shield.

However, inclusion of such openings can generally be expected to reduce the effectiveness of the radio frequency shielding in blocking the $B_1$ field and/or containing RF interference emanating from the electronic device. It is further disclosed herein to use a stack of thin sheets of electrically conductive sheets or layers (such as those shown in FIGS. 2-8) spaced apart by insulators (see FIG. 9). It is shown herein (see FIGS. 10 and 11) that as few as two mesh layers (see FIG. 2) insulated by a single insulator layer (see FIG. 9) can provide effective shielding while suppressing gradient-induced vibrations. The radio frequency shielding 50, 52 is suitably constructed of copper, or optionally may be constructed of a constructed of a lower electrical conductivity material such as a nickel-silver alloy (e.g., NiAg). The lower electrical conductivity (as compared with copper) presents a higher resistivity to the eddy currents. Thus, effective radio frequency shielding is provided while reducing mechanical vibration and other detrimental effects of eddy currents, thus reducing measurement errors and waveform distortion in patient monitors for use in the MR bore.

Techniques are disclosed herein for reducing detrimental interaction of electrical conductors with the time-varying magnetic field gradients by using electrically conductive material including openings suppressing time-varying magnetic field gradient-induced vibration of the electrical conductor. These techniques are suitably used in radio frequency shielding, or in electrically conductive enclosures generally, or in other applications which entail placement of an electrical conductor in or near an MR bore.

With reference to FIGS. 2-8, various embodiments of sheets or layers of electrically conductive material including openings suppressing time-varying magnetic field gradient-induced vibration of the radio frequency shielding 50, 52 are described.

Figure 2:
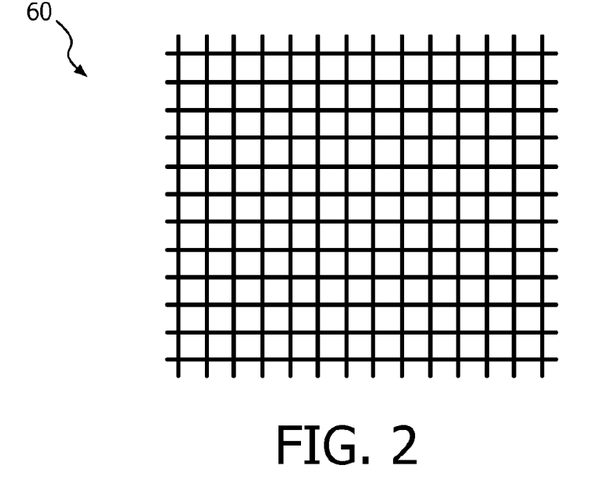
FIG. 2 diagrammatically illustrates one embodiment of electrically conductive material including openings suppressing time-varying magnetic field gradient-induced vibration of the material, wherein the material includes an electrically conductive mesh (shown in top view in FIG. 2).

FIG. 2 shows a top view of an electrically conductive sheet or layer 60 comprising an electrically conductive mesh. In this embodiment, openings of the mesh define the openings suppressing time-varying magnetic field gradient-induced vibration of the mesh 60.

Figure 3:
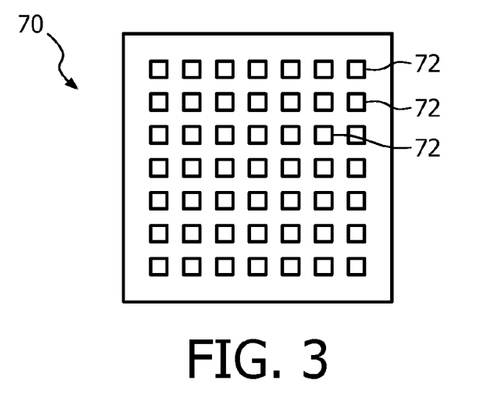
FIGS. 3, 4, and 5 diagrammatically show top views of three conductive layers or sheets including openings suppressing time-varying magnetic field gradient-induced vibration of the layer or sheet.

FIG. 3 shows a top view of an electrically conductive sheet or layer 70 in which square openings 72 are formed in a regular pattern so as to define openings suppressing time-varying magnetic field gradient-induced vibration of the layer or sheet 70. The electrically conductive sheet or layer 70 can, for example, be a metal foil into which the square openings 72 are punched, preferably using automated machinery. The openings can have other shapes besides square, such as circular, hexagonal, or so forth.

Figure 4:
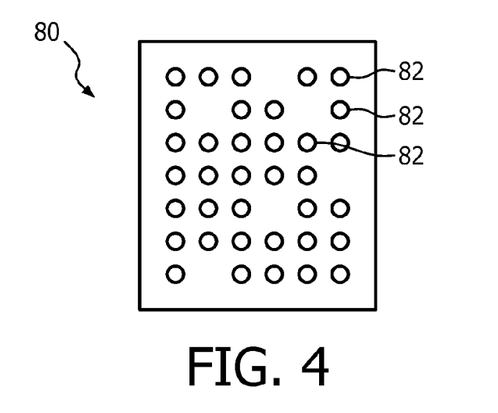

FIG. 4 shows a top view of an electrically conductive sheet or layer 80 in which circular openings 82 are formed in an irregular or random pattern so as to define openings suppressing time-varying magnetic field gradient-induced vibration of the layer or sheet 80. FIG. 4 illustrates that the openings for suppressing vibration do not need to be regularly spaced.

Figure 5:
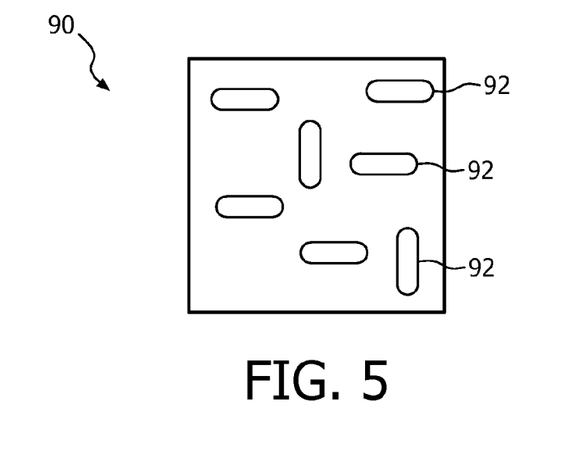

FIG. 5 shows a top view of an electrically conductive sheet or layer 90 in which slots 92 are formed in an irregular or random pattern so as to define openings suppressing time-varying magnetic field gradient-induced vibration of the layer or sheet 90. FIG. 5 illustrates that the openings for suppressing vibration do not need to be isotropic, but rather can have a large aspect ratio.

The approach of FIGS. 3-5 employs a continuous metal sheet, for example of NiAg, rather than a mesh as in the embodiment of FIG. 2. Typically, the material costs for the approach of FIGS. 3-5 is lower than the material cost for a the conductive mesh 60, and also lends itself to better handling and forming for mechanical implementation into specific radio frequency shielding structures such as the illustrative enclosure 52 or a bonded structure such as the ground plane 50 which is bonded to the circuit board 44.

Figure 6:
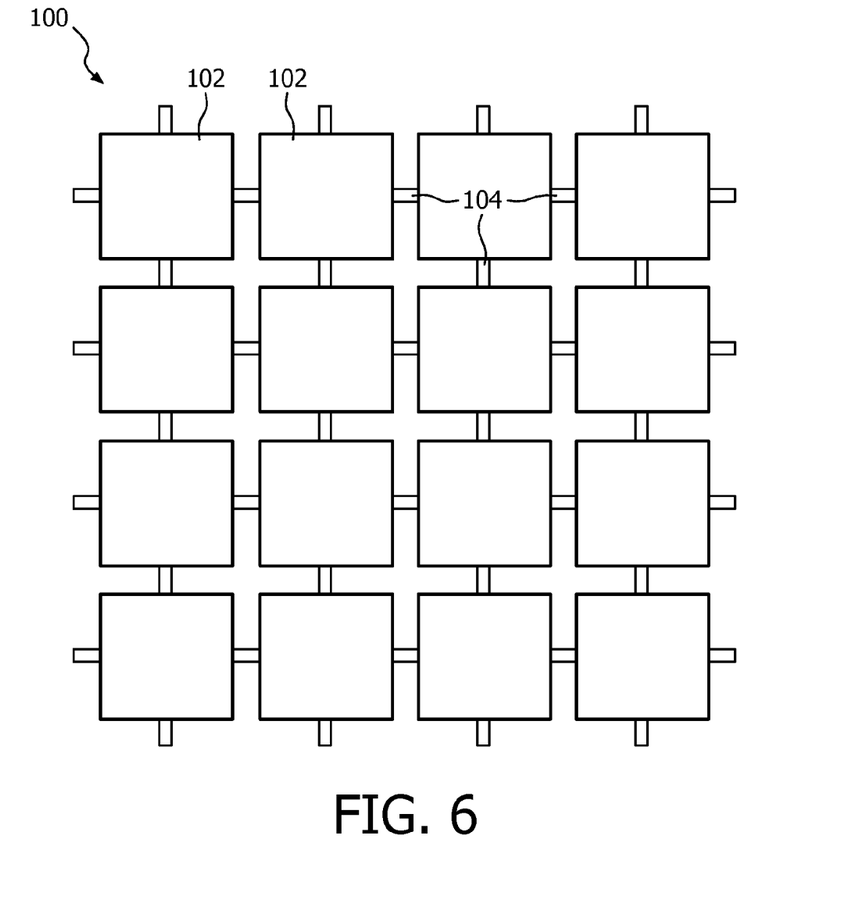
FIG. 6 diagrammatically shows a top view of a conductive layer or sheet constructed of electrically conductive elements joined by small interconnecting electrically conductive tabs so as to define openings suppressing time-varying magnetic field gradient-induced vibration of the layer or sheet.

FIG. 6 shows a top view of an electrically conductive sheet or layer 100 constructed of electrically conductive elements 102 joined by small interconnecting electrically conductive tabs 104 so as to define openings suppressing time-varying magnetic field gradient-induced vibration of the layer or sheet 100.

Figure 7:
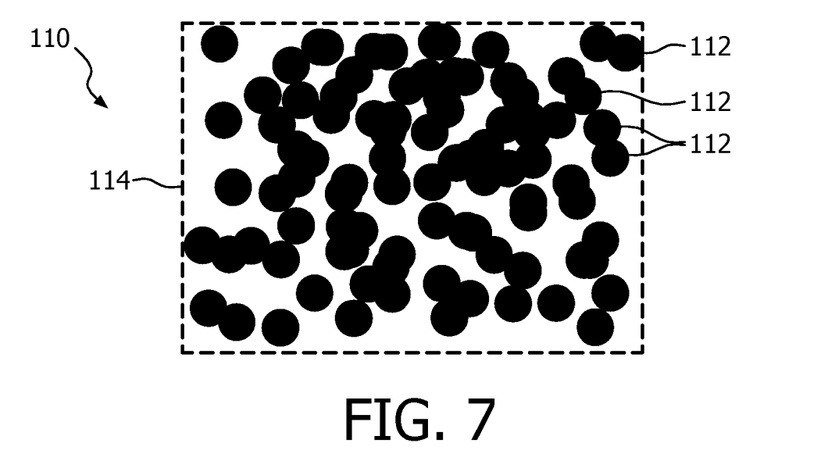
FIG. 7 diagrammatically shows a top view of a conductive layer or sheet constructed of generally contacting electrically conductive particles dispersed in an electrically insulating binder, wherein gaps between the particles define openings suppressing time-varying magnetic field gradient-induced vibration of the layer or sheet.

FIG. 7 shows a top view of an electrically conductive sheet or layer 110 constructed of generally contacting electrically conductive particles 112 dispersed in an electrically insulating binder 114, wherein gaps between the particles 112 define openings suppressing time-varying magnetic field gradient-induced vibration of the layer or sheet.

Figure 8:
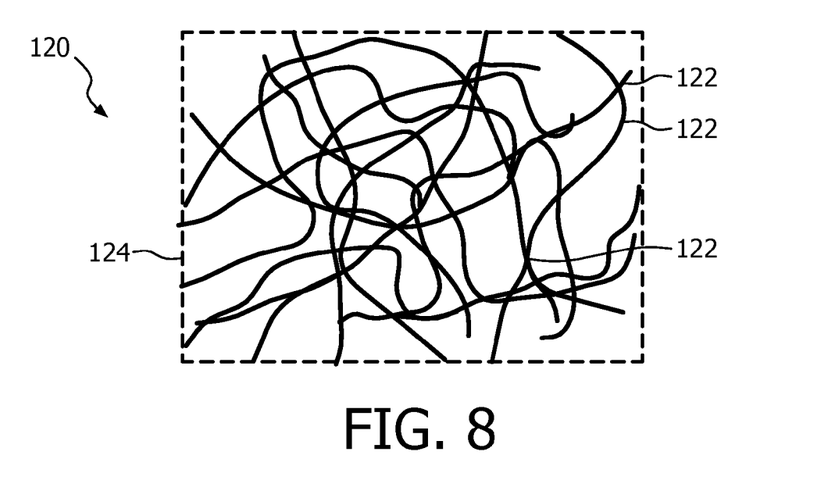
FIG. 8 diagrammatically shows a top view of a conductive layer or sheet constructed of interweaved electrically conductive fibers, wherein gaps between the fibers define openings suppressing time-varying magnetic field gradient-induced vibration of the layer or sheet.

FIG. 8 shows a top view of an electrically conductive sheet or layer 120 constructed of interweaved electrically conductive fibers 122, wherein gaps between the interweaved fibers 122 define openings suppressing time-varying magnetic field gradient-induced vibration of the layer or sheet. Optionally, the fibers 122 may be embedded or dispersed in an electrically insulating binder 124 (shown in phantom).

With continuing reference to FIGS. 2-8, the openings suppressing time-varying magnetic field gradient-induced vibration of the layer or sheet have the effect of breaking up eddy currents into small current loops, so as to dissipate the gradient energy absorbed in the shielding and reduce the eddy current-induced vibration. The size (on average) of the openings is selected to suppress the vibration while simultaneously continuing to provide acceptable radio frequency shielding. If the openings are too large the radio frequency shielding is compromised; whereas, if the openings are too small then vibration suppression is compromised.

In some embodiments, the openings of the radio frequency shielding 50, 52 are sized less than one-twentieth of the free-space magnetic resonance wavelength, which ensures effective radio frequency shielding at the magnetic resonance frequency. With the openings sized less than one-twentieth of the free-space magnetic resonance wavelength, the radio frequency shielding 50, 52 is expected to be effective for reducing radio frequency energy radiated from the electrical device or component by at least 80 decibels. The free space wavelength is c/f where $c=3.00\times10^{10}$ cm/sec is the speed of light in free space and f is the magnetic resonance frequency. By way of example, for $^1$H excitation and $B_0=1.5$ T the MR frequency is 64 MHz, and one-twentieth of the freespace wavelength is about 23 cm. For $^1$H excitation at $B_0=3.0$ T the MR frequency is 128 MHz, one-twentieth of the freespace wavelength is about 12 cm. This places an upper limit on the (average) opening size.

Another constraint on the radio frequency shielding 50, 52 is that the radio frequency shielding should have a minimum dimension that is greater than ten times a skin depth of the magnetic resonance wavelength in the electrically conductive material. This constraint imposes a minimum thickness on the conductive layer or sheet, and also indirectly imposes an upper limit on the size of the openings insofar as the openings cannot be made so large that the remaining conductive material between openings is (on average) less than ten times the skin depth of the magnetic resonance wavelength in the electrically conductive material.

On the other hand, if the openings are made on average too small then they will not be effective for suppressing eddy current-induced vibration. Typically, it is desired to reduce the time-varying magnetic field gradient-induced vibration of the radio frequency shield by at least 3 decibels. The minimum average size of the openings sufficient to provide the desired 3 decibel vibration reduction is readily determined experimentally.

In some embodiments, the opposing constraints of (i) maintaining effective radio frequency shielding (which drives toward smaller average openings) and (ii) reducing gradient-induced vibrations (which drives toward larger average openings) may be difficult to simultaneously satisfy with a single sheet or layer of conductive material such as those shown in FIGS. 2-8.

Figure 9:
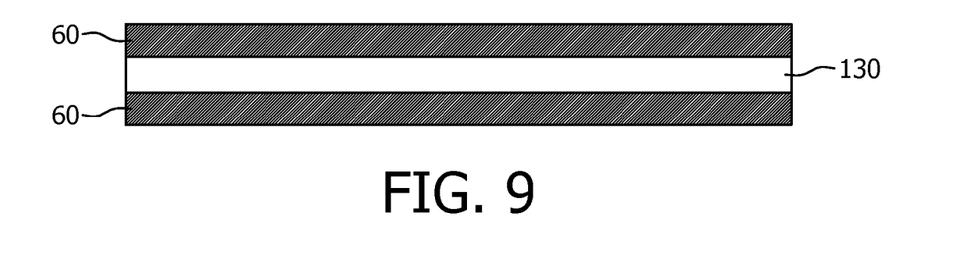
FIG. 9 illustrates a side view of two layers or sheets of electrically conductive material including openings suppressing time-varying magnetic field gradient-induced vibration of the layer or sheet (for example, any of the electrically conductive layers or sheets of FIGS. 2-6) separated by an insulating layer or sheet.

With reference to FIG. 9, in such cases it is contemplated to employ multiple layers or sheets of conductive material. FIG. 9 shows an embodiment in which two conductive layers or sheets 60, each comprising a mesh as shown in FIG. 2, are spaced apart by a dielectric layer 130. In the embodiment of FIG. 9, the two conductive layers or sheets 60 could be replaced by two conductive layers or sheets including openings suppressing time-varying magnetic field gradient-induced vibration of the radio frequency shield as shown in any of the other sheet or layer embodiments 70, 80, 90, 100, 110, 120. Moreover, while two conductive layers or sheets 60 are illustrated, separated by the dielectric layer 130, this can be extended to three conductive layers or sheets with two spacing two dielectric layers, or to four conductive layers or sheets with three spacing two dielectric layers, or more generally to N conductive layers or sheets separated by (N−1) spacing dielectric layers (where N>1). The advantageous effects of multiple sheets include: (1) further dissipating magnetic field gradient energy amongst the multiple sheets or layers; (2) increasing the electrical resistance versus a single continuous layer or sheet of the combined thickness of the constituent N conductive layers or sheets, which higher resistance reduces eddy currents; and (3) providing improved radio frequency shielding versus a single sheet.

Typically, N=2 as illustrated in FIG. 9 is expected to be sufficient. The improvement in shielding effectiveness (SE) for the double-layer ($SE_{double}$) as compared with the single layer ($SE_{single}$) is approximately $\Delta SE = SE_{double} - SE_{single} = 20 \log_{10}[(\pi \cdot l_{airgap}/\lambda_0)/|\eta/Z_\omega|]$, where $l_{airgap}$ is the thickness of the dielectric layer 130 (which is assumed to be air in this example; said another way, $l_{airgap}$ is the spacing between the two conductive layers or sheets 60 in the embodiment of FIG. 9), $Z_\omega$ is the internal impedance per unit length of mesh wires of the conductive layers or sheets 60, $\lambda_0$ is the free-space magnetic resonance wavelength, and $\eta$ is the intrinsic impedance of the conductive layers or sheets 60. See Losito, "An Analytical Characterization of Metal Foams for Shielding Applications", Progress in Electromagnetics Research Symposium, Cambridge, Mass., USA Jul. 2-6, 2008.

Figure 10:
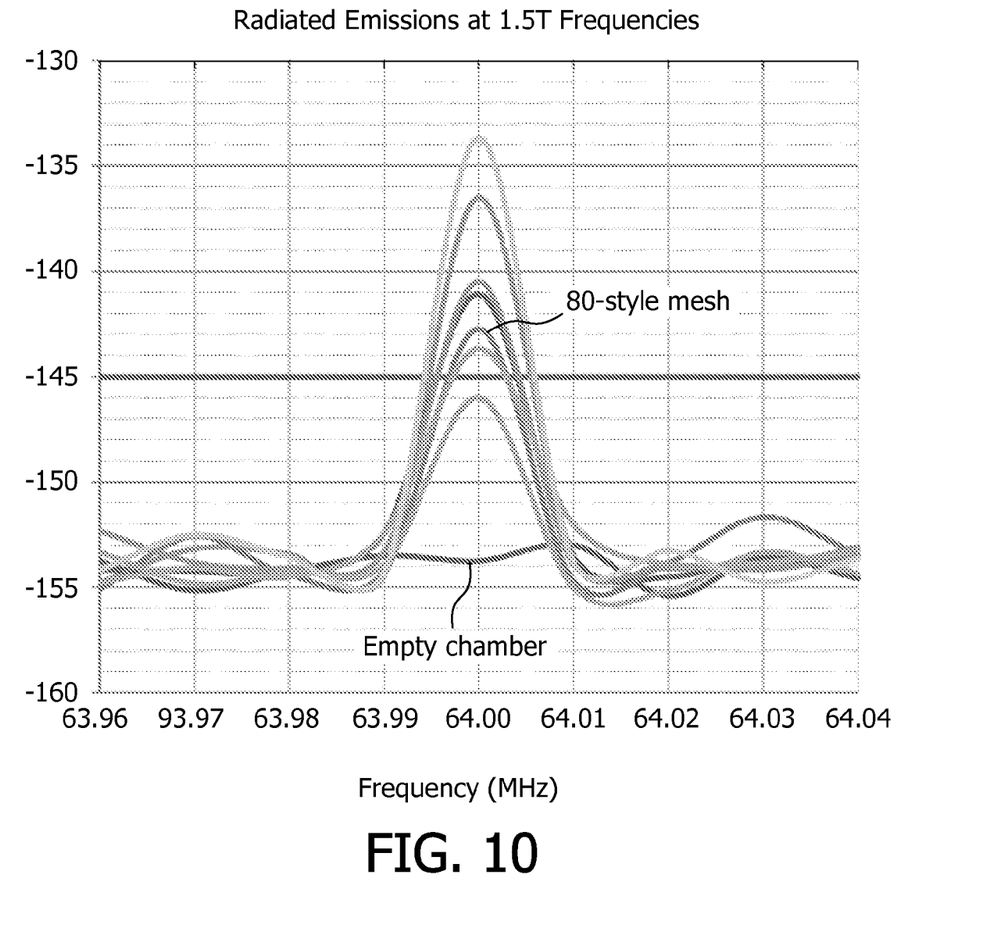
FIGS. 10 and 11 plot some experimental results as described herein.
Figure 11:
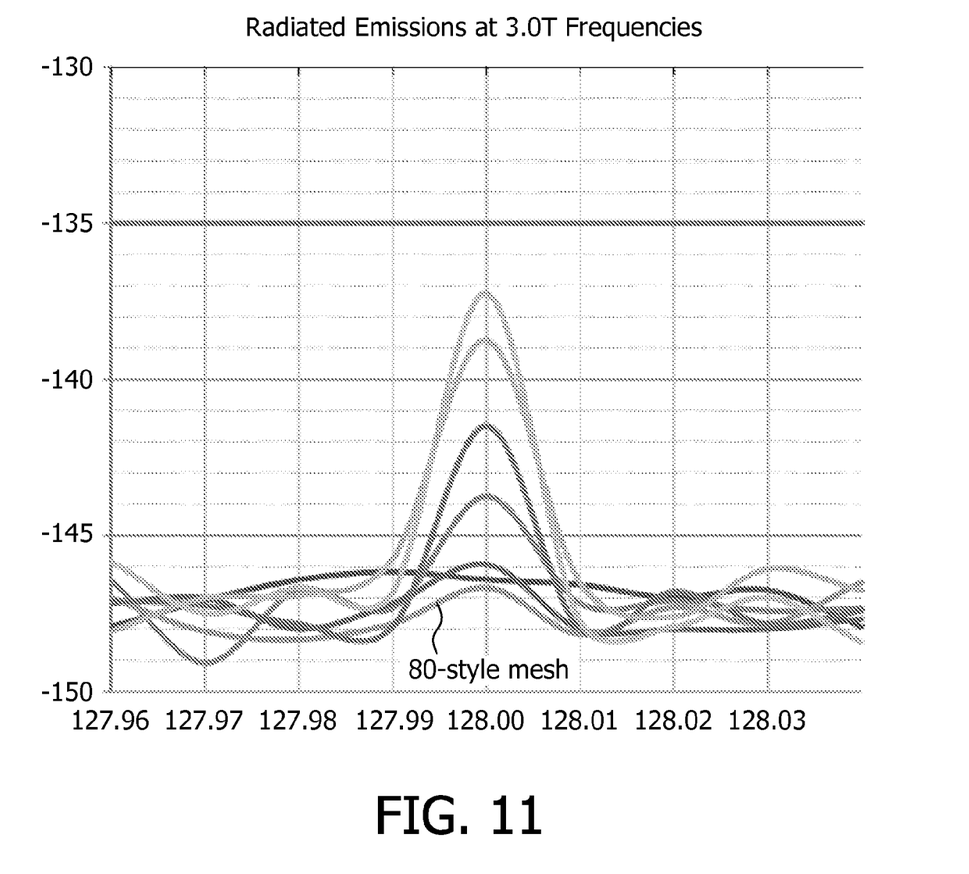

FIGS. 10 and 11 plot some experimental results for the embodiment of FIG. 2, i.e. using a single layer of the mesh 60. Radiated emissions at 1.5 T (FIG. 10) and 3.0 T (FIG. 11) were tested in the near-field using a test fixture for determining acceptable emissions levels for equipment that operates inside the bore 14. The graphs of FIGS. 10 and 11 illustrate radiated emission levels for different copper mesh sizes (20, 40, 80, and 200 OPI) and for solid Cu and NiAg layers, using a noise generator circuit at critical magnet frequencies. For near-field emissions performance of the mesh structures, there are diminishing results as aperture size gets larger and as wire diameter decreases. FIG. 11 shows that there is an optimal condition at 3.0 T where the mesh can provide more insertion loss (attenuation) at critical frequencies than the solid structure. The 80-style mesh seems to be optimal at 3.0 T.

Tests were also performed for shielding a prototype electrocardiograph (ECG) module that has been shielded using two layers of the 80-style mesh separated by a dielectric layer as per FIG. 9. Results showed that at 1.5 T frequencies, the solid shield performed about 5 dB better than the 80-style mesh, but still within acceptable limits (below −145 dB). At 3.0 T, the two-layer mesh structure of FIG. 9 provided about 10 dB more attenuation as compared with the solid shield.

This application has described one or more preferred embodiments. Modifications and alterations may occur to others upon reading and understanding the preceding detailed description. It is intended that the application be construed as including all such modifications and alterations insofar as they come within the scope of the appended claims or the equivalents thereof.

Having thus described the preferred embodiments, the invention is now claimed to be:

1. An apparatus comprising:
    an electrical device or component including a circuit board with a ground plane; and
    a radio frequency shield arranged to shield the electrical device or component, the radio frequency shield including at least the ground plane of the circuit board;
    wherein the apparatus is configured to be disposed in the bore of a magnetic resonance scanner in a radio frequency field generated by the magnetic resonance scanner and in time-varying magnetic field gradients generated by the magnetic resonance scanner; and
    wherein the ground plane of the circuit board includes an electrically conductive sheet or layer having openings sized to suppress time-varying magnetic field gradient-induced vibration of the radio frequency shield.

2. The apparatus as set forth in claim 1, wherein the radio frequency shield further comprises:
an enclosure substantially enclosing the electrical device or component.

3. The apparatus as set forth in claim 1, wherein the electrically conductive sheet or layer of the ground plane comprises an electrically conductive mesh, openings of the mesh defining the openings suppressing time-varying magnetic field gradient-induced vibration of the ground plane.

4. The apparatus as set forth in claim 1, wherein the electrically conductive sheet or layer of the ground plane comprises a metal sheet or layer having formed therein the openings suppressing time-varying magnetic field gradient-induced vibration of the ground plane.

5. The apparatus as set forth in claim 1, wherein the electrically conductive sheet or layer of the ground plane comprises electrically conductive elements joined by small interconnecting electrically conductive tabs so as to define the openings suppressing time-varying magnetic field gradient-induced vibration of the ground plane.

6. The apparatus as set forth in claim 1, wherein the electrically conductive sheet or layer of the ground plane comprises electrically conductive particles dispersed in an electrically insulating binder, gaps between the particles defining the openings suppressing time-varying magnetic field gradient-induced vibration of the ground plane.

7. The apparatus as set forth in claim 1, wherein the electrically conductive sheet or layer of the ground plane comprises interweaved electrically conductive fibers, gaps between the fibers defining the openings suppressing time-varying magnetic field gradient-induced vibration of the ground plane.

8. The apparatus as set forth in claim 1, wherein the openings of the electrically conductive sheet or layer of the ground plane are sized less than one-twentieth of the free-space magnetic resonance wavelength.

9. The apparatus as set forth in claim 1, wherein the electrically conductive sheet or layer of the ground plane has a minimum thickness greater than ten times a skin depth of the magnetic resonance wavelength in electrically conductive material of the electrically conductive sheet or layer.

10. The apparatus as set forth in claim 1, wherein the electrically conductive sheet or layer of the ground plane comprises a plurality of parallel constituent electrically conductive sheets or layers spaced apart by one or more dielectric layers.

11. The apparatus as set forth in claim 10, wherein the electrically conductive sheet or layer of the ground plane comprises two parallel constituent electrically conductive sheets or layers spaced apart by a single dielectric layer.

12. The apparatus as set forth in claim 1, wherein the radio frequency shield is effective for reducing radio frequency energy radiated from the electrical device or component by at least 80 decibels.

13. The apparatus as set forth in claim 1, wherein the openings of the electrically conductive sheet or layer of the ground plane are effective for reducing time-varying magnetic field gradient-induced vibration of the ground plane by at least 3 decibels.

14. An apparatus comprising:
a circuit board with a ground plane; and
an electrical device or component disposed on the circuit board and electrically interconnected by electrically conductive traces of the circuit board;
wherein the ground plane of the circuit board comprises an electrically conductive sheet or layer having openings sized to suppress time-varying magnetic field gradient-induced vibration of the ground plane when the apparatus is disposed in a radio frequency field generated by a magnetic resonance scanner and in time-varying magnetic field gradients generated by the magnetic resonance scanner.

15. The apparatus as set forth in claim 14, wherein the electrically conductive sheet or layer of the ground plane comprises an electrically conductive mesh, openings of the mesh defining the openings suppressing time-varying magnetic field gradient-induced vibration of the ground plane.

16. The apparatus as set forth in claim 14, wherein the electrically conductive sheet or layer of the ground plane comprises a metal sheet or layer having formed therein the openings suppressing time-varying magnetic field gradient-induced vibration of the ground plane.

17. The apparatus as set forth in claim 14, wherein the openings of the electrically conductive sheet or layer of the ground plane are sized less than one-twentieth of the free-space magnetic resonance wavelength.

18. The apparatus as set forth in claim 14, wherein the electrically conductive sheet or layer of the ground plane has a minimum thickness greater than ten times a skin depth of the magnetic resonance wavelength in electrically conductive material of the electrically conductive sheet or layer.

19. An apparatus comprising:
an electrical device or component; and
an enclosure enclosing the electrical device or component;
wherein the enclosure includes a plurality of parallel constituent electrically conductive sheets or layers spaced apart by one or more dielectric layers; and
the constituent electrically conductive sheets or layers have openings sized to suppress time-varying magnetic field gradient-induced vibration of the enclosure when the apparatus is disposed in a radio frequency field generated by a magnetic resonance scanner and in time-varying magnetic field gradients generated by the magnetic resonance scanner.

20. The apparatus as set forth in claim 19, wherein the plurality of constituent electrically conductive sheets or layers of the enclosure comprises two parallel constituent electrically conductive sheets or layers spaced apart by a single dielectric layer.

21. The apparatus as set forth in claim 14, wherein the openings of the electrically conductive sheet or layer of the ground plane are effective for reducing time-varying magnetic field gradient-induced vibration of the ground plane by at least 3 decibels.

22. A magnetic resonance system comprising:
a magnetic resonance scanner including a main magnet generating a static magnetic field in an examination region, magnetic field gradient windings for superimposing time-varying magnetic field gradients in selected directions within the examination region, and one or more radio frequency coils for generating a radio frequency field in the examination region; and
an apparatus disposed in the radio frequency field generated by the magnetic resonance scanner and in the time-varying magnetic field gradients generated by the magnetic resonance scanner, the apparatus including (i) an electrical device or component including a circuit board with a ground plane and (ii) a radio frequency shield arranged to shield the electrical device or component, the radio frequency shield including at least the ground plane of the circuit board;

wherein the apparatus is configured to be disposed in the bore of a magnetic resonance scanner in a radio frequency field generated by the magnetic resonance scanner and in time-varying magnetic field gradients generated by the magnetic resonance scanner; and wherein the ground plane of the circuit board includes an electrically conductive sheet or layer having openings sized to suppress time-varying magnetic field gradient-induced vibration of the radio frequency shield.

\* \* \* \* \*